US010624365B2

(12) United States Patent
Bruggeman et al.

(10) Patent No.: US 10,624,365 B2
(45) Date of Patent: Apr. 21, 2020

(54) COMPOSITION OF MEDIUM-CHAIN FATTY ACIDS AND FEED SUPPLEMENTED WITH COMPOSITION

(71) Applicant: NUTRITION SCIENCES N.V., Drongen (BE)

(72) Inventors: Geert Bruggeman, Bruges (BE); Katrien Deschepper, De Pinte (BE)

(73) Assignee: Nutrition Sciences N.V., Drongen (BE)

( * ) Notice: Subject to any disclaimer, the term of this patent is extended or adjusted under 35 U.S.C. 154(b) by 525 days.

(21) Appl. No.: 15/023,503

(22) PCT Filed: Oct. 9, 2014

(86) PCT No.: PCT/IB2014/065171
§ 371 (c)(1),
(2) Date: Mar. 21, 2016

(87) PCT Pub. No.: WO2015/052672
PCT Pub. Date: Apr. 16, 2015

(65) Prior Publication Data
US 2016/0213029 A1 Jul. 28, 2016

(30) Foreign Application Priority Data

Oct. 9, 2013 (BE) .................................. 2013/0672
Oct. 9, 2013 (BE) .................................. 2013/0676

(51) Int. Cl.
| A23K 10/18 | (2016.01) |
| A23K 50/75 | (2016.01) |
| A23K 50/30 | (2016.01) |
| A23K 20/105 | (2016.01) |
| A23K 50/60 | (2016.01) |
| A23K 20/158 | (2016.01) |
| A23K 50/10 | (2016.01) |

(52) U.S. Cl.
CPC ............ *A23K 10/18* (2016.05); *A23K 20/105* (2016.05); *A23K 20/158* (2016.05); *A23K 50/10* (2016.05); *A23K 50/30* (2016.05); *A23K 50/60* (2016.05); *A23K 50/75* (2016.05)

(58) Field of Classification Search
CPC ...... A23K 10/18; A23K 20/158; A23K 50/10; A23K 50/30; A23K 50/60; A23K 50/75; A23K 20/105
See application file for complete search history.

(56) References Cited

U.S. PATENT DOCUMENTS

| 3,564,098 A * | 2/1971 | Erwin et al. ......... A23K 20/105 514/556 |
| 4,225,621 A * | 9/1980 | Lanter .................. A23K 20/105 426/2 |
| 5,208,257 A | 5/1993 | Kabara |
| 5,462,967 A * | 10/1995 | Hayashi ................. A61K 31/23 426/2 |
| 6,635,303 B1 | 10/2003 | Youcheff et al. |
| 6,638,978 B1 | 10/2003 | Kabara |
| 7,261,888 B1 | 8/2007 | Decuypere et al. |
| 9,271,517 B2 | 3/2016 | Bruggeman et al. |
| 2003/0176500 A1* | 9/2003 | Molly .................... A01N 37/02 514/547 |
| 2005/0100584 A1 | 5/2005 | Miller et al. |
| 2007/0219270 A1 | 9/2007 | Bruggeman |
| 2009/0275657 A1 | 11/2009 | Dee et al. |
| 2010/0058651 A1* | 3/2010 | Knuth ...................... A23D 9/00 44/385 |
| 2010/0098802 A1* | 4/2010 | Navarro ................. A61K 31/19 426/2 |
| 2012/0041065 A1* | 2/2012 | Appleby ................ A23K 50/80 514/558 |
| 2013/0199452 A1* | 8/2013 | Gordon .................... A01K 5/00 119/51.03 |
| 2013/0224320 A1* | 8/2013 | Campmany ............ A61K 31/23 424/776 |
| 2014/0357718 A1* | 12/2014 | Feuerstein ............. A61K 31/19 514/558 |
| 2015/0025145 A1* | 1/2015 | Hollander .............. A23K 50/80 514/558 |
| 2016/0205970 A1 | 7/2016 | Bruggeman et al. |

FOREIGN PATENT DOCUMENTS

| CA | 2727663 A1 * | 7/2012 | ............ A23K 10/30 |
| EP | 1106077 A1 | 6/2001 | |
| GB | 2342292 A * | 4/2000 | .......... A61K 31/341 |
| JP | 08-175989 A | 7/1996 | |
| WO | WO-9966804 A1 * | 12/1999 | .......... A23K 20/158 |
| WO | WO 2006/002927 A2 | 1/2006 | |
| WO | WO 2008/061078 A2 | 5/2008 | |
| WO | WO 2013/184879 A2 | 12/2013 | |

OTHER PUBLICATIONS

Young, JAOCS, vol. 60(2) 1983, pp. 374-379 (Year: 1983).*
Machine translation of CA2727663 (Year: 2011).*
Jensen, J. Dairy Sci. 85:295-350 (Year: 2002).*
Caro et al., "Enzymatic synthesis of medium-chain triacylglycerols by alcoholysis and interesterification of copra oil using a crude papain lipase preparation," *European Journal of Lipid Science Technology*, vol. 106(8), pp. 503-512 (2004).
Nair et al., "Antibacterial Effect of Caprylic Acid and Monocaprylin on Major Bacterial Mastitis Pathogens," *Journal of Dairy Science*, American Dairy Science Association, vol. 88(10), pp. 3488-3495 (Oct. 1, 2005).
Hill et al. Fatty acid intake alters growth and immunity in milk-fed calves. J. Dairy Sci. 94, pp. 3936-3948 (2011 ).

(Continued)

*Primary Examiner* — C. Sayala
(74) *Attorney, Agent, or Firm* — Knobbe, Martens, Olson & Bear, LLP

(57) ABSTRACT

The present invention relates to a composition containing medium-chain fatty acids or salts or mono-, di-, triglycerides, esters or amides derivatives of medium-chain fatty acids for use as a feed additive for animals, in an optimized ratio. In a second and third aspect, the invention concerns an animal feed, supplemented with the composition containing the medium-chain fatty acids or derivatives and a method for feeding animals with the animal feed.

10 Claims, No Drawings

(56) References Cited

OTHER PUBLICATIONS

Piepers et al. Oral supplementation of medium-chain fatty acids during the dry period supports the neutrophil viability of peripartum dairy cows. J. Dairy Res. 80, pp. 309-318 (Apr. 2013).
Van Meenen, E. Vitamex presentation: Effects of Medium Chain Fatty Acids on Rumen Fermentation. EAAP 2009, Barcelona (2009).
Van Meenen, E. Oral supplementation of medium chain fatty acids for better immunity. Int. Dairy Topics 10(1), p. 11 (2011).

* cited by examiner

COMPOSITION OF MEDIUM-CHAIN FATTY ACIDS AND FEED SUPPLEMENTED WITH COMPOSITION

CROSS-REFERENCE TO RELATED APPLICATIONS

This application is the U.S. National Phase under 35 U.S.C. § 371 of International Application PCT/IB2014/065171, filed Oct. 9, 2014, which claims priority to BE2013/0672, filed Oct. 9, 2013 and BE2013/0676, filed Oct. 9, 2014.

TECHNICAL FIELD

The present invention relates to a composition for use as feed additive and animal feed comprising medium-chain fatty acids for the improvement of the intestinal health and immunity of animals, as well as for the elimination of harmful pathogens.

STATE OF THE ART

The optimization of animal feed efficiency, the damming of infections and the animal growth that is directly related to this can have a significant influence on, among other things, the ecological footprint of the meat industry. There is a need for measures that can reduce high feed costs and decrease maintenance costs of food-producing animals. This will also directly lead to the optimization of the profits. Feed additives can offer to be important tool. These can help in the fight against pathogenic infections and can effect a positive influence on, for example, the feed conversion.

The positive characteristics of medium-chain fatty acids as a feed additive composition for animals have previously been known. EP 1 294 37 and EP 1 765 318 both describe a feed, supplemented with a feed additive consisting of medium-chain fatty acids having 6 to 10 carbon atoms. These additives have both a positive influence on the reduction or elimination of microbial pathogens in the gastrointestinal tract of animals. CN 1 016 422 01 describes a feed additive, specifically for pigs, consisting of medium-chain fatty acids, phospholipids, and lipases, the food additive having a positive effect on the digestion of the animals.

Caro et al. (2004) describes a methodology to obtain a mixture, via enzymatic synthesis, of medium-chain fatty acids from coconut oil.

EP 1 314 358 also discloses the use of compositions of medium-chain fatty acids for use in, among other things poultry and pigs.

However, the current state of the art describes primarily a composition with only one or a few chain-fatty acids. In addition, these compositions often, if they comprise multiple medium-chain fatty acids, offer non-optimal ratios and are not well balanced. A good balancing of the composition of feed additives on the basis of different medium-chain fatty acids is, however, crucial. After all, a non-optimal or suboptimal concentration of the medium-chain fatty acids may have the result that it is less or even not effective when used in a feed additive composition.

Another problem with the feed additive on the basis of medium-chain fatty acids is related to the strong, unpleasant smell of some of these medium-chain fatty acids or derivatives, as experienced by the animals. Thus, an animal will not be or be less inclined to eat a non-optimally balanced composition.

It is the object of the present invention to provide a composition with an optimal composition of medium-chain fatty acids, an optimal ratio between the mutual medium fatty acids, ensuring both the efficient intake of the medium-chain fatty acids, as well as that the ratios between the individual fatty acid chains are optimized. Thus, an optimal effect is obtained. Furthermore, it is also the object of the present invention to provide a composition that has a broad antibacterial effect and can be used for a large group of species. Thus, the composition may offer a valid alternative to the often frequent use of antibiotics in agriculture industry.

SUMMARY OF THE INVENTION

The present invention relates to a composition including medium-chain fatty acids comprising free fatty acids of caproic acid (C6), caprylic acid (C8), capric acid (C10) and lauric acid (C12) or salts, thereof in an amount of at least 20% by weight of said composition, wherein the ratio between the sum of caprylic acid, capric acid and lauric acid (C8+C10+C12) or salts, thereof and the total sum of medium-chain fatty acids (C8) and lauric acid (C12) is more than 1 or wherein the composition further comprises vitamins, trace elements or carboxylic acids and/or salts thereof, selected from the group consisting of valeric acid, formic acid, acetic acid, propionic acid, lactic acid, butyric acid, citric acid, maleic acid, fumaric acid, benzoic acid, succinic acid, sorbic acid, and tartaric acid and an animal feed wherein the inclusion amount of the composition in the feed is between 0.01 and 0.2% by total weight of the feed. Thus, the present invention aims to offer a solution to inhibit, eliminate, excrete, kill off, regulate and/or monitor enteropathogens by means of administration of a composition, for example as a feed additive or feed, comprising a balanced ratio of medium-chain fatty acids. The concentration of various medium-chain fatty acids, and the mutual ratio between them was determined by the inventors in such a way that the individual fatty acid chains show a synergistic effect. Consequently, the activity of the composition according to the present invention is optimized.

In a further aspect, the present invention relates to a method for feeding comprising administering a feed comprising the composition, wherein the animal obtains the composition in an amount of between 0.1 and 200 mg/kg body weight/day, in order to improve the health of an individual, to increase the weight gain, to increase the daily nutritional intake, to decrease the feed conversion and to generally increase the well-being by means of administrating the composition of the feed as herein described according to the invention.

DETAILED DESCRIPTION

The invention relates to a composition with an optimal ratio of medium-chain fatty acids, suitable for use as feed additive in an animal feed. The composition is optimized such that the medium-chain fatty acids exhibit a synergistic effect. The composition according to the present invention therefore has a broad antimicrobial effect. In particular, the composition will have an inhibiting and/or reducing effect on pathogens, involved in infections of the gastrointestinal tract.

Accordingly, the present invention offers a solution for the treatment of such infections. The composition of the present invention will also have a beneficial effect on the overall immunity of the animals fed with the feed comprising the composition. Unless defined otherwise, all terms used in the description of the invention, including technical and scientific terms, have the meaning as they are commonly understood by the skilled person in the technical field of the invention. The following terms are explicitly explained for a better assessment of the description of the invention.

"A", "an" and "the" refer in this document to both the singular and the plural, unless the context clearly implies otherwise. For example, "a segment" means one or more than one segment.

Where "approximately" or "about" is used in this document with a measurable quantity, a parameter, a time period or time, and the like, then variations are intended of +/−20% or less, preferably +/−10% or less, more preferably +/−5% or less, even more preferably +/−1% or less, and even more preferably +/−0.1% or less than the value cited, to the extent that such variations are applicable in the described invention. However, it should be understood that the value of the quantity with which the term "approximately" or "about" is used, is specifically disclosed in itself.

The terms "comprise", "comprising", "consist of", "consisting of", "provided", "include", "including", "contain", "containing", "hold", "holding" are synonyms and are inclusive or open terms that indicate the presence of what follows, and which do not exclude or prevent the presence of other components, characteristics, elements, members, steps, as known from or disclosed in the state of the art. The citation of numeric interval by the endpoints includes all integer numbers, fractions, and/or real numbers between the endpoints, these endpoints included.

In a first aspect, the invention relates to a composition comprising medium-chain fatty acids or salts, such as $NH_4^+$—, $Na^+$—, $K^4$— and/or $Ca^{2+}$-salts, mono-, di-, triglycerides, esters or amides thereof for use as feed additive in animals. As described herein, the term "medium-chain fatty acids" or "MCFA" refers to fatty acids with a medium-chain length, wherein the fatty acids may be saturated or unsaturated. According to the invention, the MCFAs can consist of 6 to 12 carbon atoms, in particular, caproic acid (C6), caprylic acid (C8), capric acid (C10) or lauric acid (C12).

Preferentially, this composition comprises a mixture of medium-chain fatty acids, whereby these preferably have a chain length of 6 to 12 carbon atoms. In particular, the composition will comprise medium-chain fatty acids, selected from the group, consisting of caproic acid (C6), caprylic acid (C8), capric acid (C10) and lauric acid (C12).

In one embodiment, the medium-chain fatty acids are chemically modified, and the medium-chain fatty acids are provided with side-chains, such as, without limitation, one or more alkyl groups, preferably C1-C10 alkyl groups, in particular methyl or ethyl groups.

In a further embodiment, the present invention comprises derivatives of medium-chain fatty acids. As described herein, the term "derivative of a medium-chain fatty acid" refers to a fatty acid chain of which the carboxyl group is reversibly converted to a different group, preferably, but without limitation, to an amide, salt, ester or glyceride. As described herein, the term "free fatty acids" refers to fatty acids that are not converted into a salt or a derivative (such as an amide, ester or glyceride). The use of esters and salts, for example, prevents the diffusion of bad odors, which may occur when the free fatty acids are used.

The use of C6 to C12 medium-chain fatty acids in animal feed and for the promotion of the gastrointestinal tract is known in the state of the art. However, often it concerns merely adding a certain concentration of medium-chain fatty acids, without substantially taking into account the importance of the mutual ratios between the different fatty acid chains.

The ratios between the various medium-chain fatty acids of present invention was so determined as to obtain an optimum, even synergistic activity. The term "ratio" from the present invention should be understood as a ratio between the amounts of medium-chain fatty acids, and can be interpreted as either a weight or volume ratio.

The composition will preferably comprise caprylic acid (C8) and capric acid (C10) or derivatives thereof, the ratio of caprylic acid (C8) to capric acid (C10) being at least 0.6 and/or maximum 2. The inventors of the present invention found that this ratio between caprylic acid and capric acid resulted in a synergistic effect, especially with regard to the pursued objectives.

The composition will, in a preferred embodiment, also include lauric acid (C12) or a derivative thereof. Preferably, the proportion of caprylic acid will be higher in the composition than the proportion of lauric acid. More preferably, lauric acid and caprylic acid will also be present in a specific ratio in the composition. In a preferred embodiment, the ratio of caprylic acid (C8) and lauric acid (C12) will be more than 1 (C8/C12>1).

Also, in a preferred embodiment, the composition according to the present invention comprises caproic acid (C6). Preferably, the ratio between the sum of caprylic acid, capric acid, and lauric acid (C8+C10+C12) and the total sum of the medium-chain fatty acids in the composition will be more than 0.8. In particular, it will be ((C8+C10+C12)/(C6+C8+C10+C12)>0.8).

In a preferred embodiment:
the ratio C8/C10 will be between 0.6 and 2 and the ratio (C8+C10+C12)/(C6+C8+C10+C12) will be more than 0.8; or
the ratio C8/C12>1 and (C8+C10+C12)/(C6+C8+C10+C12)>0.8.

In a most preferred embodiment, the composition will comprise caproic acid (C6), caprylic acid (C8), capric acid (C10) and lauric acid (C12), wherein the ratio between caprylic acid (C8) and capric acid (C10) is at least 0.6 and maximum 2, wherein the ratio of caprylic and lauric acid C8/C12 is more than 1 and wherein (C8+C10+C12)/(C6+C8+C10+C12)>0.8.

In other words, in a preferred embodiment will be:
0.6<(C8/C10)<2.0 and C8/C12>1.0 and (C8+C10+C12)/(C6+C8+C10+C12)>0.8.

It has been found that ratios that fall outside of these boundary values result in only a sub-optimal or even strongly reduced efficacy of the composition. In support, we refer to Example 1 and the results shown in Table 1.

In another embodiment, the composition will preferably comprise at least caprylic acid (C8) and capric acid (C10) or a derivative thereof, and at least one other medium-chain fatty acid or derivative thereof selected from the group consisting of lauric acid (C12) and caproic acid (C6). Preferably, the composition also includes, in addition to caprylic acid and capric acid, lauric acid (C12) and caproic acid (C6) or a derivative thereof.

In one embodiment, the ratio between the sum of caprylic acid (C8) and capric acid (C10) or derivative thereof, and the sum of the total fatty acid chains or derivatives thereof will at least amount to 0.5.

In another preferred embodiment, the ratio between the sum of caprylic acid and capric acid (C8+C10) and the sum of lauric acid and caproic acid (C12+C6) will be at least 2.5. In another embodiment, the ratio between the sum of caprylic acid and capric acid (C8+C10) and the sum of lauric acid and caproic acid (C12+C6) will amount to maximum 90.

In a preferred embodiment, the composition according to the present invention comprises C6, C8, C10 and C12 medium-chain fatty acids or their derivatives (salts, mono-, di-, triglycerides, esters or amides) in a following ratio:

2.5<(C8+C10)/(C6+C12)<90.

The most preferred embodiment of the composition of the present invention comprises C6, C8, C10 and C12 medium-chain fatty acids or their derivatives (salts, mono-, di-, triglycerides, esters or amides) in the following ratio:

(C8+C10)/(C6+C8+C10+C12)>0.5 and 2.5<(C8+C10)/(C6+C12)<90.

These ratios were found to be an optimal efficacy and exhibited efficiency. In support, we refer to Example 2 and 3 and the results shown in Table 2 and 3.

In another preferred embodiment, the composition according to the present invention has a combination of the above ratios. In an embodiment, the composition will meet the following parameters:

0.6<(C8/C10)<2.0 and C8/C12>1.0 and (C8+C10+C12)/(C6+C8+C10+C12)>0.8 and (C8+C10)/(C6+C8+C10+C12)>0.5 and 2.5<(C8+C10)/(C6+C12)<90.

The ratios of medium-chain fatty acids in the composition of the present invention also allows for suppression of potential enteric pathogens; without however disturbing the pH balance in the gastro-intestinal tract. The gastrointestinal tract comprises the stomach, with a pH of between 3 and 4, the large intestine, having a pH between 6 and 7 and the small intestine having a pH of around 7. Micro-organisms, such as pathogens, as well as neutral or beneficial microorganisms are mainly present in the small and large intestine. An optimal balance between these groups of micro-organisms is essential for the health of the animals, and in particular for the prevention of infections of the gut. Here, it is important that each part of the gastro-intestinal tract maintains a proper pH, and that the microbial balance is also maintained.

In one embodiment, the composition or the feed is provided with the composition according to the invention as described herein, is used for the selective elimination, suppression or regulation of one or more enteropathogens, selected from the group consisting of filamentous micro-organisms and micro-organisms with adhesion structures, Gram-negative bacteria, Gram-positive bacteria, fungi, yeast, and viruses. The term "(entero) pathogens," as opposed to "beneficial or non-pathogenic gastrointestinal microbial flora" means herein micro-organisms which have a detrimental effect on the host, and in particular which cause diseases or ailments. Other forms of adverse effects are a reduced daily food intake, reduced daily weight gain, increased feed conversion, and reduced overall health and wellness.

In a further embodiment, the enteropathogens are selected from the group consisting of the bacterial pathogens of the genera *Brachispira, Vibrio, Escherichia, Salmonella* (such as, without limitation, *Salmonella typhimurium, Salmonella enteritidis* and *Salmonella java*), *Shigella, Klebsiella, Erwinia, Yersinia, Campylobacter* (such as, without limitation, *Campylobacter jejuni, Campylobacter coli, Campylobacter laris*, and *Campylobacter upsaliensis*), *Helicobacter, Pseudomonas, Enterococcus* and *Clostridium*; preferably *Brachyspira hyodysenteriae*; fungal and yeast pathogens of the genera *Penicillium, Aspergillus, Fusarium, Cephalosporum, Saccharomyces, Candida, Fungi Imperfecti* and *Hemiascomycetes*; and viral pathogens of the genera *Norovirus* and *Rotavirus*.

In one embodiment, the composition of the present invention is active against both Gram-positive and Gram-negative bacteria. Preferably, the composition of the present invention is effective against species of the genus *Staphylococcus, Salmonella* or *Escherichia*.

In another preferred embodiment, the composition according the present invention is extremely suitable for the control of *Clostridium* sp. infections (such as, without limitation, *Clostridium novyi, Clostridium tetani, Clostridium perfringens, Clostridium tertium* and *Clostridium histolyticum*) in human and animal, preferably into the gastrointestinal tract of animals.

The composition of medium-chain fatty acids according to the present invention may operate in several ways. In a first instance, they will suppress (inhibit) or eliminate pathogenic microorganisms in the gastrointestinal tract, reducing the risk of infections. In this case preferably only the enteropathogens are killed and removed, while the favorable or non-pathogenic gastro-intestinal bacterial flora (such as for example, *Lactobacillus*) is maintained. In a second instance, the reduction in microbial activity in the gastro-intestinal tract will ensure a decrease in the feed conversion ratio. The feed conversion ratio is a measure of the efficiency with which the animal is able to convert a certain amount of food or mass into body weight, and can be defined as the amount of food consumed divided by the gain in body weight, over a specific time. A decrease in the feed conversion ratio is thus linked to improved feed efficiency in the animal. The composition of the present invention will also be suitable for the decontamination of feed or the elimination of pathogens present in food (so-called food borne pathogens).

In particular, the composition of the present invention and the feed, supplemented with this composition, will also provide an improved intestinal flora and will increase the overall immunity in animals.

In one embodiment, the composition or the feed according to the invention as described herein is administered to animals which are selected from the group consisting of fish, amphibians, reptiles, birds, and mammals, such as, without limitation, adult or juvenile ruminant animals, sheep, goats, cattle, pigs, horses, poultry, fowl, domestic animals (e.g. dogs, cats, rabbits, hamsters, guinea pigs), and preferably selected from the group consisting of poultry, pigs and ruminants. In one embodiment, the composition or the feed is administered to pigs (for example, fattening pigs, piglets, sows, . . . of all ages and types). The formula here provides unique antimicrobial, physiological and immunological properties. By supplementation of the composition to the feed of the pig, the microflora and the mucosa are positively impacted, resulting in an improved health and zootechnical performance.

In pigs, this will also lead to a better feed conversion with better growth efficiency, better meat growth, and improved health (as there is effected a positive effect on the immune system).

In another embodiment, the composition is suitable for administration to poultry, and the feed, supplemented with this composition, provides an improved intestine and increase of the overall immunity in animals. In poultry, this will also result in a better feed conversion with improved growth efficiency, improved egg production and increase of meat production. In yet another embodiment, the composition is administered to ruminants (incl. calves).

It can be generally stated that the composition according to the present invention is suitable for improving the zootechnical performance of pigs, poultry, and/or ruminant animals (including cattle, dairy cattle, calves . . . ).

In one embodiment, the composition according to the invention, as described herein, comprises additional raw materials (additives) and/or growth-promoting substances. The additives are, in a preferred embodiment, selected from the group consisting of aroma's and plant extracts. In a further preferred embodiment, the growth-promoting components are selected from the group, consisting of antibiotics, vitamins, trace elements, probiotics, prebiotics, essential oils, enzymes, fatty acids, and (in)organic acids. Non-limiting examples of organic acids which can be used in an embodiment of the invention, comprise C1-C12 carboxylic acids, in particular unsubstituted carboxylic acids such as formic acid, acetic acid, propionic acid, butyric acid and valeric acid; and/or substituted carboxylic acids such as adipic acid, maleic acid, succinic acid, citric acid, fumaric acid, tartaric acid, lactic acid, gluconic acid, succinic acid and ascorbic acid, including cyclic carboxylic acids such as picolinic acid. The organic acids may contain one or more substituted or unsubstituted carboxylic acids, as well as mixtures thereof, as well as saturated, unsaturated, cyclic, and/or aliphatic carboxylic acids or mixtures thereof, as well as metal complexes and/or salts thereof, as well as racemic and/or enantiomeric forms thereof. Non-limiting examples of inorganic acids which can be used in an embodiment of the invention include strong acids in small amounts, such as perchloric acid (hydroperchloric acid), hydrogen iodide, hydrogen bromide (hydrobromic acid), hydrogen chloride (hydrochloric acid), sulfuric acid and nitric acid; as well as weak inorganic acids such as phosphoric acid, hydrofluoric acid, hypochlorous acid, and nitrous acid.

In one embodiment, the medium-chain fatty acids in the composition according to the invention are present in liquid or solid form. In a further embodiment, the feed additive according to the invention as described herein, is formulated as a liquid or a solid form. The term "solid form" means a powder in particular. The term "liquid form", in particular, means a solution in water or means a solution in oil. The medium-chain fatty acids as described herein according to the invention are oil-soluble and can be provided both as powder and as an oil-solution.

In one embodiment, the concentration of the medium-chain fatty acid, as described herein, amounts at least 1, 5, 10, 15, 20, 25, 30, 35, 40, 45, 50, 55, 60, 65, 70, 75, 80, 85, 90, 95, 99% by weight of the composition. In a further embodiment, the medium-chain fatty acids, as described herein, amounts to (based on dry weight) between 1 g/100 g composition (1% by weight) and 100 g/100 g composition (100% by weight), preferably between 50 g/100 g and 90 g/100 g composition (50-90% by weight), more preferably between 60 g/100 g and 80 g/100 g. This is to mean that the concentration of the MCFAs such as described herein maximally amounts to 100% by weight of the composition.

In a second aspect, the present invention includes an animal feed, supplemented with the compositions according to the invention.

Preferably, the animal feed of the invention comprises up to 10% by weight of the medium-chain fatty acids (or salts, derivatives, or mixtures), as described herein. In particular the inclusion amount of the composition in the feed, will preferably be between 0.01 and 0.5%; more in particular will be between 0.01 and 0.2% by total weight of the feed. More preferably, the inclusion amount will be between 0.05 and 0.15%, most preferably it is 0.1%. In a further embodiment, the feed comprises an amount of medium-chain fatty acids (or salts, derivatives, or mixtures), as described herein (based on dry weight) of between 0.01 g/100 g of dietary supplement (0.01% by weight) and 1 g/100 g of a dietary supplement, (1% by weight), preferably 0.07 g/100 g of food supplement (0.07% by weight).

Conventional animal feeds naturally possess no or only a minimal amount of free medium-chain fatty acids. Addition of the composition of the present invention to the animal feed results in an animal feed which comprises medium-chain fatty acids (MCFA).

Consequently, the feed according to the present invention will comprise, after supplementation with a composition according to an embodiment of the present invention, at least caprylic acid (C8) and capric acid (C10). Preferably, the ratio between caprylic acid (C8) and capric acid (C10) in the feed will amount to at least 0.6. In a further embodiment, this ratio will amount to maximum 2. In a further aspect, the feed also comprises lauric acid (C12). Preferably, the content of caprylic acid in the composition will be more than the level of lauric acid. Preferably, the ratio between caprylic and lauric acid will be more than 1.

In a further preferred embodiment, the feed will also comprise caproic acid (C6) after supplementation. Preferably, the ratio between the sum of caprylic acid, capric acid, and lauric acid (C8+C10+C12) and the sum of caproic acid, caprylic acid, capric acid, and lauric acid (C6+C8+C10+C12), in the feed is more than 0.8. In particular, it will be $0.6<(C8/C10)<2.0$ and $C8/C12>1.0$, and $(C8+C10+C12)/(C6+C8+C10+C12)>0.8$.

In another preferred embodiment, an animal feed according to the present invention will at least comprise caprylic acid (C8) and capric acid (C10), wherein the ratio between the sum of caprylic acid and capric acid (C8+C10), and the total amount of MCFA in the feed is at least 0.5.

Preferably, the supplemented feed also includes lauric acid (C12) and caproic acid (C6), wherein the ratio between the sum of caprylic acid and capric acid (C8+C10) and the sum of lauric acid and caproic acid (C12+C6) in the feed is at least 2.5, and/or maximum 90.

In a most preferred embodiment, the feed according to the present invention will comprise C6, C8, C10 and C12 medium chain fatty acids or their derivatives (salts, mono-, di-, triglycerides, esters or amides), in following ratio:
$(C8+C10)/(C6+C8+C10+C12)>0.5$ and $2.5<(C8+C10)/(C6+C12)<90$.

Preferably, the inclusion amount of the composition will ensure that an animal that has been fed with the animal feed, obtains the composition in an amount of between 0.1 and 200 mg/kg body weight/day of the animal, more preferably obtains between 0.1 and 100 mg/kg body weight of the animal/day.

In a third aspect, the present invention also comprises a method for feeding animals, with an animal feed, supplemented with a composition according to the present invention, wherein the animal obtains the composition in an amount of between 0.1 and 200 mg/kg body weight/day of the animal, more preferably between 0.1 and 100 mg/kg body weight of the animal/day.

Preferably, the daily dose of the feed will be provided in an uptake of the composition between 1 and 100 mg/kg body weight/day. Preferably, the animal is fed on a daily basis.

In what follows, the invention is described by means of non-limiting examples which illustrate the invention, and which are not intended nor should be construed to limit the scope of the invention.

EXAMPLES

Example 1

Five times three samples of 100 ml culture medium (specific for each pathogen) were simultaneously inoculated with an overnight culture of respectively *E. coli* K88 (Gram-negative pathogen in the gastrointestinal tract of piglets), *S. typhimurium* (Gram-negative zoonotic germ in the gastrointestinal tract of piglets) and *Streptococcus* sp. (Gram-positive pathogen in the gastrointestinal tract of piglets) and further incubated at 37° C. The optical density was measured at 600 nm ($OD_{600\ nm}$, proportional to the amount of microbial cells present). Once an $OD_{600\ nm}$ between 0.2 and 0.5 was achieved, the following ratios of MCFAs were added to a 0.1% dose in the feed:

(1) nothing was added to the first sample with a specific strain, (2) a ratio (C8+C10+C12)/(C6+C8+C10+C12)=0.70 was added to the second sample* with specific strain (3) a ratio (C8+C10+C12)/(C6+C8+C10+C12)=0.80 was added to the third sample* with specific strain (4) a ratio (C8+C10+C12)/(C6+C8+C10+C12)=0.90 was added to the fourth sample* with specific strain (5) a ratio (C8+C10)/(C6+C8+C10+C12)=0.99 was added to the fifth sample* with specific strain

* wherein the ratio C8/10 is 1, and the ratio of C8/C12 was 1.5 in all treatments.

The samples were further incubated at 37° C. for 4 hours at a pH of 4.0. Incubation was put to a halt after 4 hours. The $OD_{600\ nm}$ was measured at time 0 h and after 4 h. Results of this measurement are shown in Table 1.

TABLE 1a

Antimicrobial effect ("+" is an observed anti-microbial effect, "−" is no observed effect) with specific (C8 + C10 + C12)/(C6 + C8 + C10 + C12)) ratios as compared to pathogenic micro-organisms (both Gram-negative and Gram-positive)

| | Ratio | | | | |
|---|---|---|---|---|---|
| Strain | 0 | 0.7 | 0.8 | 0.9 | 0.99 |
| *E. coli* K88 | − | − | − | + | + |
| *S. typhimurium* | − | − | − | + | + |
| *Streptococcus* | − | − | − | + | + |

TABLE 1b

Antimicrobial effect ("+" is an observed anti-microbial effect, "−" is no observed effect) with specific (C8 + C10)/(C6 + C8 + C10 + C12) ratios of pathogenic micro-organisms (both Gram-negative and Gram-positive)

| Strain | C8/C10 = 1 | C8/C12 = 1.5 | (C8 + C10 + C12)/(C6 + C8 + C10 + C12)** |
|---|---|---|---|
| *E. coli* K88 | − | − | + |
| *S. typhimurium* | − | − | + |
| *Streptococcus* | − | − | + |

**Ratios 0.9, C8/C10 being the ratio 1 and C8/C12 being the ratio 1.5.

From Table 1a and 1b can be clearly deduced that the ideal ratio (C8+C10+C12)/(C6+C8+C10+C12) for anti-bacterial efficacy must be higher or equal to 0.80. Moreover, there is a synergistic effect between respectively C8+C10+C2 and C6+C8+C10+C12.

Example 2

Six samples of 100 ml culture medium (specific for each pathogen) were simultaneously inoculated with an overnight culture of Clostridial sp. (Gram-positive pathogen in the gastrointestinal tract of piglets as well as poultry), and further incubated at 37° C. The optical density was measured at 600 nm ($OD_{600\ nm}$, proportional to the amount of microbial cells present). Once an $OD_{600\ nm}$ between 0.2 and 0.5 was achieved, the following ratios of MCFAs were added to a 0.1% dose in the feed:

(1) nothing was added to the first sample with *Clostridium* sp., (2) a ratio (C8+C10)/(C12+C6)=2.5 was added to the second sample * with *Clostridium* sp.

(3) a ratio (C8+C10)/(C12+C6)=5 was added to the third sample * with *Clostridium* sp.

(4) a ratio (C8+C10)/(C12+C6)=10 was added to the fourth steel * with *Clostridium* sp.

(5) a ratio (C8+C10)/(C12+C6)=90 was added to the fifth steel * with *Clostridium* sp.

(6) a ratio (C8+C10)/(C12+C6)=95 was added to the sixth steel * with *Clostridium* sp.

* wherein the ratio (C8+C10)/(C6+C8+C10+C12) are 0.9 in all treatments

The samples were further incubated at 37° C. for 4 hours at a pH of 4.0. Incubation was put to a halt after 4 hours. The $OD_{600\ nm}$ was measured at time 0 h and after 4 h. Results of this measurement are shown in Table 2.

TABLE 2 anti-microbial effect ("+" is anti-microbial effect, "−" is no antimicrobial effect) of specific (C8 + C10)/(C12 + C6) ratios on *Clostridium* sp. at a final dose or 0.1% based on the culture base

| | ratio | | | | | |
|---|---|---|---|---|---|---|
| Strain | 0 | 2.5 | 5 | 10 | 90 | 95 |
| *Clostridium* | − | − | + | + | + | − |

Example 3

Comparison of MCFA, Ratios for Control and Inhibition of Pathogens

Three samples of 100 ml culture medium (specific for each pathogen) were simultaneously inoculated with an overnight culture of Clostridial sp. (Gram-positive pathogen in the gastrointestinal tract of piglets as well as poultry), and further incubated at 37° C. The optical density was measured at 600 nm ($OD_{600\ nm}$, proportional to the amount of microbial cells present). Once an OD600 nm between 0.2 and 0.5 was obtained, respectively C8+C10, C6+C12, and (C8+C10)/(C6+C12) were added to a 0.1% dose of the culture base.

TABLE 3 anti-microbial effect of respectively C8 + C10, C6 + C12 and (C8 + C10)/(C6 + C12) with *Clostridium* at a final dose of 0.1% on culture base

| Stam | C8 + C10 | C6 + C12 | (C8 + C10)/(C6 + C12)** |
|---|---|---|---|
| *Clostridium* | − | − | + |

**ratio = 50

From Tables 2 and 3 it is clear that the ideal ratio (C8+C10)/(C12+C6) for anti-microbial action lies between 2.5 and 90. In addition, there was a synergistic effect observed between C8+C10 and C6+C12.

What is claimed is:

1. A feed for an animal comprising a feed suitable for the animal and a feed additive composition, wherein the composition comprises medium-chain fatty acids comprising free fatty acids of caproic acid (C6), caprylic acid (C8), capric acid (C10) and lauric acid (C12) or salts, thereof in an amount of at least 20% by weight of said composition,
   wherein the ratio between the sum of caprylic acid, capric acid and lauric acid (C8+C10+C12) or salts, thereof and the total sum of medium-chain fatty acids or salts, thereof in the composition is 0.9 or more,
   wherein a ratio between caprylic acid (C8) and lauric acid (C12) is more than 1,
   and wherein the inclusion amount of the composition in the feed is between 0.01 and 0.2% by total weight of the feed.

2. Animal feed according to claim 1, wherein the inclusion amount of the composition ensures that an animal, fed with the animal feed, obtains the composition in an amount of between 0.1 and 200 mg/kg body weight/day of the animal.

3. Method for improving the intestinal flora in animals comprising administering the composition of claim 1 to the animal.

4. Method for enhancing immunity in animals comprising administering the composition of claim 1 to the animal.

5. Method for increasing the feed efficiency in an animal comprising administering the composition of claim 1 to the animal.

6. Method for feeding animals comprising administering a feed comprising the composition of claim 1, wherein the animal obtains the composition in an amount of between 0.1 and 200 mg/kg body weight/day.

7. Method for feeding animals according to claim 2, characterized in that the daily dose of the feed provides for an uptake of the composition between 0.1 and 200 mg/kg body weight/day of the animal.

8. Method according to claim 6, wherein the animal is fed on a daily basis.

9. Method according to claim 6, wherein the animals are poultry, pigs or ruminants.

10. Composition according to claim 1, wherein the composition further comprises vitamins, trace elements or carboxylic acids and/or salts thereof, selected from the group consisting of valeric acid, formic acid, acetic acid, propionic acid, lactic acid, butyric acid, citric acid, maleic acid, fumaric acid, benzoic acid, succinic acid, sorbic acid, and tartaric acid.

* * * * *